US012227545B2

United States Patent
Wang et al.

(10) Patent No.: US 12,227,545 B2
(45) Date of Patent: Feb. 18, 2025

(54) ACINETOBACTER BAUMANNII IMMUNOGENIC PROTEIN AND COMPOSITION AND APPLICATION THEREOF

(71) Applicant: CHENGDU OLYMVAX BIOPHARMACEUTICALS INC., Chengdu (CN)

(72) Inventors: Hengliang Wang, Beijing (CN); Li Zhu, Beijing (CN); Chao Pan, Beijing (CN); Zhicheng Liu, Beijing (CN); Xin Li, Beijing (CN); Jun Wu, Beijing (CN); Peng Sun, Beijing (CN); Ming Zeng, Beijing (CN); Bin Wang, Beijing (CN); Xiankai Liu, Beijing (CN); Dongshu Wang, Beijing (CN); Erling Feng, Beijing (CN)

(73) Assignee: CHENGDU OLYMVAX BIOPHARMACEUTICALS INC., Chengdu (CN)

( * ) Notice: Subject to any disclaimer, the term of this patent is extended or adjusted under 35 U.S.C. 154(b) by 1076 days.

(21) Appl. No.: 17/058,527

(22) PCT Filed: May 23, 2019

(86) PCT No.: PCT/CN2019/088074
§ 371 (c)(1),
(2) Date: Nov. 24, 2020

(87) PCT Pub. No.: WO2019/223749
PCT Pub. Date: Nov. 28, 2019

(65) Prior Publication Data
US 2021/0214400 A1 Jul. 15, 2021

(30) Foreign Application Priority Data
May 24, 2018 (CN) .......................... 201810510029.2

(51) Int. Cl.
| | |
|---|---|
| *A61K 39/104* | (2006.01) |
| *A61K 39/39* | (2006.01) |
| *A61P 31/04* | (2006.01) |
| *C07K 14/21* | (2006.01) |
| *C07K 16/12* | (2006.01) |
| *A61K 39/00* | (2006.01) |

(52) U.S. Cl.
CPC ........ *C07K 14/212* (2013.01); *A61K 39/1045* (2013.01); *A61K 39/39* (2013.01); *A61P 31/04* (2018.01); *C07K 16/1218* (2023.08); *A61K 2039/55544* (2013.01); *C07K 2319/55* (2013.01)

(58) Field of Classification Search
None
See application file for complete search history.

(56) References Cited

U.S. PATENT DOCUMENTS

2016/0361406 A1 12/2016 Yang

FOREIGN PATENT DOCUMENTS

| CN | 106511994 A | 3/2017 |
|---|---|---|
| CN | 108503698 A | 9/2018 |

OTHER PUBLICATIONS

Davos et al., (Proteins: Structure, Function and Genetics, 2000, vol. 41: 98-107).*
Wisstock et al., (Quarterly Reviews of Biophysics 2003, vol. 36 (3): 307-340.*
Mikayama et al. (Nov. 1993. Proc.Natl.Acad.Sci. USA, vol. 90 : 10056-10060).*
Stratmann, T. (Vaccines (Basel). Sep. 2015; 3(3): 579-596).*
Bentancor, Leticia V. et al.; "Identification of Ata. a Multifunctional Trimeric Autotransporter of *Acinetobacter baumannii*"; Journal of Bacteriology, vol. 194, No. 15, published May 18, 2012; pp. 3950-3960.
Smith, M.G., et al.; "Hypothetical Protein AIS_1032 [*Acinetobacter baumannii* ATCC 17978]"; GenBank: AB011464.2 {from https://www.ncbi.nlm.nih.gov], Jan. 31, 2014; 2 pages.
International Search Report received in corresponding International Application No. PCT/CN2019/088074; National Intellectual Property Administration, PRC; Jul. 4, 2019; 7 pages.
Written Opinion received in corresponding International Application No. PCT/CN2019/088074; National Intellectual Property Administration, PRC; Jul. 4, 2019; 9 pages.
First Office Action issued in corresponding Chinese Application No. 201810510029.2; mailed Jun. 1, 2020; State Intellectual Property Office of the P.R. China, Beijing, China; 32 pgs.

(Continued)

*Primary Examiner* — Jennifer E Graser
(74) *Attorney, Agent, or Firm* — HAUPTMAN HAM, LLP

(57) ABSTRACT

The present invention discloses a *Acinetobacter baumannii* immunogenic protein and its composition and application. This invention provides a protein, comprising 39 amino acids of the N-terminal α-helix part of the Ata protein transport functional domain of *Acinetobacter baumannii* and an adjuvant protein; amino acid sequence of said 39 amino acids of the N-terminal α-helix part of the Ata protein transport functional domain of *Acinetobacter baumannii* is shown as the $127^{th}$-$165^{th}$ amino acid residues of SEQ ID NO:2. In present invention the 39 amino acids of the N-terminal α-helix part of surface protein Ata (*Acinetobacter* trimeric autotransporter) of *Acinetobacter baumannii*, was took to fuse with CTB, and express in BL21. The protein was purified by a nickel column, and used to intraperitoneally immunize mouses by 2.5 μg/mouse. Its immunogenicity and immunoprotection was verified through the animal experiments, which proves it has a good effect of anti-infection of *Acinetobacter baumannii*.

3 Claims, 2 Drawing Sheets

Specification includes a Sequence Listing.

(56) References Cited

OTHER PUBLICATIONS

Bentancor, Leticia V. et al.; "Evaluation of the Trimeric Autotransporter Ata as a Vaccine Candidate against *Acinetobacter baumannii* Infections"; Infection and Immunity, vol. 80, No. 10, published Sep. 11, 2012; pp. 3381-3388.

Wei, Zhenbo et al.; "Cloning, expression and antigen immune protection study of an outer membrane protein of severe infective *Acinetobacter baumannii*"; Immunological Journal, vol. 31, No. 5, published May 2015; pp. 380-385, English abstract only provided.

\* cited by examiner

ACINETOBACTER BAUMANNII IMMUNOGENIC PROTEIN AND COMPOSITION AND APPLICATION THEREOF

RELATED APPLICATIONS

The present application is a National Phase of International Application Number PCT/CN2019/088074 filed May 23, 2019 and claims priority to Chinese Application Number 201810510029.2 filed May 24, 2018.

INCORPORATION BY REFERENCE

The sequence listing provided in the file entitled NWB20825_sequence_listing_rev2.txt which is an ASCII text file that was created on Mar. 26, 2021, and which comprises 3,291 bytes, is hereby incorporated by reference in its entirety.

TECHNICAL FIELD

The invention relates to the field of biotechnology, especially relates to *Acinetobacter baumannii* immunogenic protein and its composition and application, in particular, it relates to an immunogenic fusion protein comprising a component of *Acinetobacter baumannii* Ata protein, a vaccine composition containing the protein, and application thereof in a method for immunizing animals or humans to resist *Acinetobacter baumannii* infection.

BACKGROUND

*Acinetobacter baumannii* (Ab) is a gram-negative bacterium that exists widely in nature. It is a kind of opportunistic pathogenic bacteria. It is highly susceptible to infections in people with weakened immune functions. It is also one of the most typical clinical pathogens in hospital infections. Because of its fast proliferation and strong adhesion, it is widely distributed in the hospital environment, and with the large-scale use of antibiotics, more and more drug-resistant strains have appeared. *Acinetobacter baumannii* has posed a serious threat to the global healthcare system. At present, antibiotics are mainly used clinically to combat *Acinetobacter baumannii* infection.

However, because of the emergence of multi-drug resistant strains, the doctors have to combine medication during treatment. But there are many disadvantages in combination medication. Therefore, the development of related vaccines is urgent for preventing the epidemic of *Acinetobacter baumannii*. Unfortunately, there is no vaccine against *Acinetobacter baumannii* on the market.

Therefore, there is an unmet need for immunogenic proteins that can be used to prepare vaccines against *Acinetobacter baumannii* and vaccines containing the proteins.

SUMMARY

The present invention aims to provide an immunogenic fusion protein containing a fragment of *Acinetobacter baumannii* Ata protein, a vaccine composition containing the protein and its application in a method for immunizing mammals against *Acinetobacter baumannii* infection.

Through in-depth experimental research, the inventors of the present invention found that the fusion protein, formed by component of the surface protein Ata (*Acinetobacter* trimeric autotransporter) of *Acinetobacter baumannii* fused with the adjuvant protein, has immunogenicity that meets the requirements of vaccines for *Acinetobacter baumannii* and can be used to prepare the vaccine for preventing *Acinetobacter baumannii* infection and apply the vaccine. Based on the above findings, the inventors completed the present invention.

The present invention can be described from different aspects. The inventions described in these aspects and any of their forms are independent and related to each other, and they combine with each other to constitute the content of the present invention.

One aspect of the present invention provides an immunogenic fusion protein comprising a component of the Ata protein of *Acinetobacter baumannii*, the component comprising the amino acid sequence fragment of the N-terminal α-helix part of the Ata protein transport functional domain of *Acinetobacter baumannii*; and adjuvant protein or protein fragment with adjuvant function.

Another aspect of the present invention provides a nucleic acid molecule encoding the aforementioned fusion protein.

Another aspect of the present invention provides a biomaterial selected from:
1) An expression cassette containing the aforementioned nucleic acid molecule;
2) A recombinant vector containing the aforementioned nucleic acid molecule; and
3) Recombinant bacteria or transgenic cell lines containing the aforementioned nucleic acid molecule.

Another aspect of the present invention provides a method for protecting animals or humans from infection of *Acinetobacter baumannii*, comprising the following steps: immunize animals or humans in need with aforementioned protein composition or the aforementioned fusion protein or the aforementioned nucleic acid molecule or the aforementioned biomaterial to achieve resistance to *Acinetobacter baumannii* infection.

Another aspect of the present invention provides a method for producing *Acinetobacter baumannii* antibodies, comprising the following steps: effectively immunize animals or humans with aforementioned protein composition or the aforementioned fusion protein or the aforementioned nucleic acid molecule or the aforementioned biomaterial to obtain *Acinetobacter baumannii* antibodies.

Aforementioned immunization may be intraperitoneal immunization or subcutaneous immunization.

Another aspect of the present invention provides a product comprising the aforementioned protein or the aforementioned protein composition or the aforementioned fusion protein or the aforementioned nucleic acid molecule or the aforementioned biomaterial or the aforementioned antibodies.

Another aspect of the present invention provides the use of the fusion protein of the present invention or its encoding nucleic acid molecule in preparing a vaccine composition against *Acinetobacter baumannii* infection.

EMBODIMENTS

Figure 1:
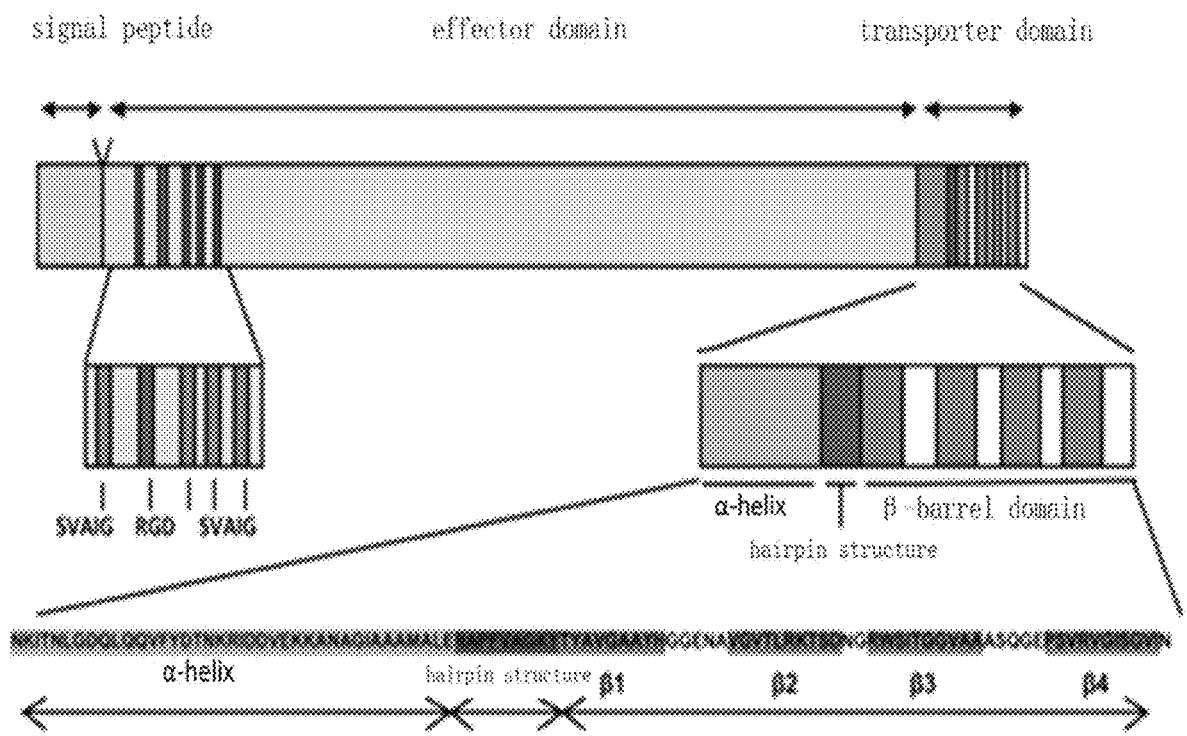
FIG. 1 is a schematic diagram of the 39 amino acids in the N-terminal α-helix part of the protein Ata transport functional domain.

The present invention has been outlined above, and examples will be given below to further describe the present invention in detail.

In order to accurately understand the terms used in the present invention, the meanings of some terms are specifically defined below. For terms that are not specifically defined herein, they have the meaning generally understood and accepted by those skilled in the art. If the meaning of a term defined herein is inconsistent with the meaning generally understood and accepted by those skilled in the art, the meaning of the term shall be subject to the meaning defined herein.

The term "protein" used in the present invention refers to molecular chains of amino acids, including peptides, oligopeptides and polypeptides. If necessary, the said protein can be modified in vivo or in vitro by, for example, glycosylation, amidation, carboxylation or phosphorylation. The protein or peptide can be natural or synthetic.

The term "fusion protein" as used in the present invention means a protein formed by two or more polypeptides that are directly or indirectly covalently linked to each other in a certain manner.

The term "immunoprotecting" as used in the present invention means the response ability (partially or fully) of serum antibodies and/or cytotoxic T cell induced during immunization, which prevents diseases caused by such as *Acinetobacter baumannii*.

The term "homology" used in the present invention refers to the homology of DNA nucleotide and protein amino acid sequences. The former can be determined by DNA sequencing methods, and the latter can be determined by methods such as mass spectrometry or Edman degradation.

According to one aspect of the present invention, there is provided an immunogenic protein composition comprising 39 amino acids of the N-terminal α-helix part of the Ata protein transport functional domain of *Acinetobacter baumannii* and an adjuvant protein or protein fragment with adjuvant function.

According to another aspect of the present invention, there is provided an immunogenic fusion protein, which comprises a component of *Acinetobacter baumannii* Ata protein, this component contains the 39 amino acids of the N-terminal α-helix part of the Ata protein transport functional domain of *Acinetobacter baumannii*, that is, the $127^{th}$-$165^{th}$ amino acid residues in SEQ ID NO:2; and an adjuvant protein or protein fragment with adjuvant function.

In one embodiment, the adjuvant protein is specifically the cholera toxin B subunit, namely CTB protein.

In another embodiment, the aforementioned fusion protein is any protein of the following a)-e):
  a) A protein whose amino acid sequence comprises the amino acid sequence shown in SEQ ID NO:2 in the sequence listing;
  b) The amino acid sequence consists of the amino acid residues shown in SEQ ID NO:2 in the sequence listing;
  c) A protein obtained by substituting and/or deleting and/or adding one or several amino acid residues in the amino acid sequence defined in a) or b), which has the function of improving animal immunity;
  d) A protein that has more than 99%, more than 95%, more than 90%, more than 85%, or more than 80% homology with the amino acid sequence defined by a) or b) and has the function of improving animal immunity;
  e) A fusion protein obtained by attaching a tag to the N-terminal and/or C-terminal of the protein defined in any one of a)-d).

According to another aspect of the present invention, there is provided a nucleic acid molecule encoding the aforementioned fusion protein, and the nucleic acid molecule is a nucleic acid molecule shown in any of the following 1)-4):
  1) Its coding sequence includes SEQ ID NO:1 in the sequence listing;
  2) Its coding sequence is SEQ ID NO:1 in the sequence listing;
  3) DNA molecule that hybridizes with the DNA molecule defined in 1) or 2) under stringent conditions and encodes the aforementioned proteins;
  4) DNA molecule that has more than 80% or more than 90% homology with the DNA molecule defined in 1) or 2) and encodes the aforementioned proteins.

According to another aspect of the present invention, there is provided a biomaterial selected from:
  1) An expression cassette containing the aforementioned nucleic acid molecule;
  2) A recombinant vector containing the aforementioned nucleic acid molecule;
  3) Recombinant bacteria or transgenic cell lines containing the aforementioned nucleic acid molecule.

According to another aspect of the present invention, there is provided an application of the said protein, aforementioned protein composition, aforementioned fusion protein, aforementioned nucleic acid molecule or the biomaterial in at least one of the following 1)-6):
  1) Prepare products that promote animals or humans to produce antibodies against *Acinetobacter baumannii*;
  2) Prepare products for the prevention and/or treatment of diseases caused by *Acinetobacter baumannii*;
  3) Prepare products resistant to infestation or infection by *Acinetobacter baumannii*;
  4) Promote animals or humans to produce antibodies against *Acinetobacter baumannii*;
  5) Prevent and/or treat diseases caused by *Acinetobacter baumannii*;
  6) Resist infestation or infection by *Acinetobacter baumannii*.

According to another aspect of the present invention, there is provided a method for making animals or humans resistant to infection by *Acinetobacter baumannii*, which comprises the following step: immunize animals or humans with the protein or protein composition or fusion protein or nucleic acid molecule or biomaterial of any of the aforementioned schemes to achieve resistance to *Acinetobacter baumannii* infection.

According to another aspect of the present invention, there is provided a method for producing *Acinetobacter baumannii* antibodies, which comprises the following steps: immunize animals or humans with the protein or protein composition or fusion protein or nucleic acid molecule or biomaterial of any of the aforementioned schemes to obtain the *Acinetobacter baumannii* antibodies.

The antibodies prepared by aforementioned methods are also protected by the present invention.

The application of the aforementioned antibodies in at least one of the following 1)-6) is also within the protection scope of the present invention:
1) Prepare products that promote animals or humans to produce antibodies against *Acinetobacter baumannii*;
2) Prepare products for the prevention and/or treatment of diseases caused by *Acinetobacter baumannii*;
3) Prepare products resistant to infestation or infection by *Acinetobacter baumannii*;
4) Promote animals or humans to produce antibodies against *Acinetobacter baumannii*;
5) Prevent and/or treat diseases caused by *Acinetobacter baumannii*;
6) Resist infestation or infection by *Acinetobacter baumannii*.

According to another aspect of the present invention, a product is provided, which comprises the protein or protein composition or fusion protein or nucleic acid molecule or biomaterial or antibodies of any of the aforementioned embodiments.

In one embodiment, the product of the present invention has at least one of the following a-c functions: a) Promote animals or humans to produce antibodies against *Acinetobacter baumannii*; b) Prevent and/or treat diseases caused by *Acinetobacter baumannii*; c) Resist infestation or infection by *Acinetobacter baumannii*.

In one embodiment, said product is medicine or health product or detection kit or vaccine.

In one embodiment, said animal is mouse.

To further illustrate the present invention, the following examples are provided. These examples are only used to illustrate the present invention, and should not constitute any limitation to the present invention.

The experimental methods used in the following examples are conventional methods unless otherwise specified.

The materials and reagents used in the following examples can be obtained from commercial sources unless otherwise specified.

Example 1. Obtaining the Fusion Protein CTB-Ata

Fusion protein CTB-Ata comprises CTB amino acid sequence and 39 amino acids of the N-terminal α-helix part of the surface protein Ata (*Acinetobacter* trimeric autotransporter) transport functional domain of *Acinetobacter baumannii*.

1. Fusion Protein CTB-Ata

For the surface protein Ata (*Acinetobacter* trimeric autotransporter) of *Acinetobacter baumannii*, the 39 amino acids (FIG. 1) of the N-terminal α-helix part of its transport functional domain were taken and used.

Then, the 39 amino acids of the α-helix part of the Ata protein, the tac promoter, and the CTB protein for fusion expression were synthesized by whole gene to form the fusion protein CTB-Ata. The amino acid sequence of the fusion protein is shown as SEQ ID NO:2 in the sequence listing.

The $20^{th}$-$123^{rd}$ amino acids residues in SEQ ID NO:2 represent the fusion expressed CTB protein, the $127^{th}$-$165^{th}$ amino acids residues represent the α-helix part of Ata protein, and the $201^{th}$-$206^{th}$ amino acids residues represent the His tag.

The nucleotide sequence of the fusion protein encoding gene CTB-Ata is shown as SEQ ID NO:1 in the sequence listing, in which nt103-131 is the tac promoter, nt235-543 is the coding gene for CTB protein, and nt556-672 is the coding gene for alpha-helix part of Ata protein, and nt778-795 is the His tag gene.

2. The Vector for Expressing the Fusion Protein CTB-Ata

Digested PET28a(+) (NOVAGEN company, catalog number: 69864) with XbaI and XhoI to obtain a large vector fragment. Connected aforementioned fusion protein coding gene CTB-Ata shown in SEQ ID NO: 1 to the large vector fragment to obtain the recombinant expression vector pET28a-CTB-Ata.

The recombinant expression vector pET28a-CTB-Ata is a vector obtained by replacing the DNA molecule between the XbaI and XhoI restriction sites of the pET28a(+) vector with the fusion protein encoding gene CTB-Ata shown in SEQ ID NO: 1. This fusion protein contains His tag of the vector.

3. Expression and Purification of Fusion Protein CTB-Ata

The recombinant expression vector pET28a-CTB-Ata obtained in aforementioned 2 was introduced into BL21 cells to obtain recombinant strain pET28a-CTB-Ata/BL21.

The recombinant strain pET28a-CTB-Ata/BL21 was inoculated into 5 ml LB liquid medium containing a final concentration of 50 μg/mL kanamycin, cultivated overnight at 37° C., and passaged in LB liquid medium at a volume ratio of 1:100, cultivated at 37° C. until $OD_{600}$ was about 0.6, added IPTG with a final concentration of 1 mM, reduced the temperature to 30° C. and induced for 12 hours, obtained protein induction culture solution, centrifuged (10800 g for 8 minutes), collected the precipitate to obtain protein induction bacteria.

Took 30 g of protein induction bacteria, added 100 ml A1 solution (20 mM pH7.5 Tris-HCl, 0.5M NaCl, 10 mM imidazole, adjusted the pH to 7.0), ultrasonically broke the bacteria (ultrasonic 4 s and pause 5 s, cumulatively ultrasonic 2 h), centrifuged at 12 000 g, collected the supernatant which was the crude extract containing the fusion protein CTB-Ata.

The aforementioned supernatant was purified using a Chelating affinity chromatography column (GE Healthcare, product catalog number 17-5203-06) (Φ 1.6 cm*15 cm). First flushed the column bed with 0.5M NaOH aqueous solution for at least 3 column beds volume, then balanced with deionized water to neutral pH, then used 0.5M $NiSO_4$ aqueous solution to equilibrate at least 3 column beds volume. Then equilibrated at least one column bed volume with B1 solution (20 mM pH7.5 Tris-HCl, 0.5M NaCl, 500 mM imidazole, adjusted the pH to 7.0), and finally balanced at least 3 column beds volumes with the aforementioned A1 solution, and the flow rate of above steps was 4 mL/min. Loaded the crude extract by the A pipeline, then washed the unbound protein with A1 solution, and rinsed until the UV absorption (280 nM) was close to 0 mAU. Finally, linear elution was carried out with a solution containing 0%-100% (volume ratio) of B1 solution (A pipeline loaded A1 solution, B pipeline loaded B1 solution, and the purifier automatically mixed), collected 80 mL of eluate, and obtained a purified fusion protein CTB-Ata.

Figure 2:
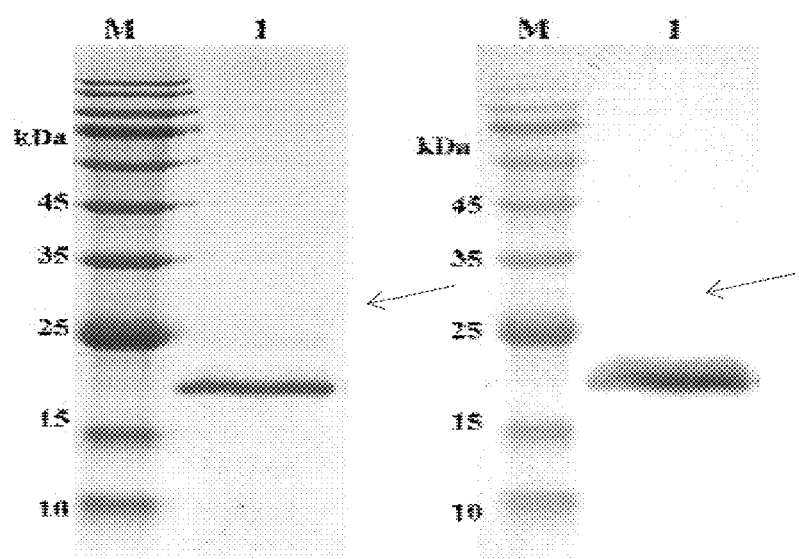
FIG. 2 is the SDS-PAGE analysis result of the purified fusion protein CTB-Ata.

The purified fusion protein CTB-Ata was analyzed by 15% SDS-PAGE and detected by WB with anti-His antibodies. The result is shown in FIG. 2. After purification, a relatively pure target fusion protein CTB-Ata (molecular weight 22.5 kDa) was successfully obtained. After protein quantification by BCA method, the following animal experiments were carried out.

The empty vector pET28a was transferred into BL21 cells, and the expression was induced in the same way, but the target protein was not obtained.

Example 2. Functional Verification of the Fusion Protein CTB-Ata

1. Animal Immunity

Diluted the purified fusion protein CTB-Ata prepared in Example 1 with physiological saline to prepare an immune sample containing the fusion protein CTB-Ata. The immunization was carried out according to the immunization dose of 2.5 μg of fusion protein CTB-Ata per mouse (mouse weight was about 17 g), and immunization with the Ata peptide fragment (39 amino acids of N-terminal α-helix part) was as a control.

Took 50 5-week-old female Balb/c mice (Beijing Vital River Laboratory Animal Technology Co. Ltd) (with no significant difference in body weight) and randomly divided them into 5 groups (10 mice in each group):

Two groups of intraperitoneal immunization: each mouse was injected with 100 μl of immunization sample containing the fusion protein CTB-Ata (CTB-ATA (intraperitoneal)) or Ata peptide (ATA (intraperitoneal)), the immunization dose was 2.5 μg per mouse.

Two groups of subcutaneous immunization: each mouse was injected with 100 μl of immunization sample containing the fusion protein CTB-Ata (CTB-ATA (subcutaneous)) or Ata peptide (ATA (subcutaneous)), the immunization dose was 2.5 μg per mouse.

Blank control group (no sample injected, control): female Balb/c mice.

Each group was immunized on the 1st, 14th, and 28th day. After each immunization injection, cut the tail and collected blood, and collected the serum of each group of mice.

2. Titer Detection of Antibody Against *Acinetobacter baumannii*

The indirect ELISA method was used to detect the titer of antibody against *Acinetobacter baumannii* in the serum of each group of mice, details as follows:

The expression vector pGEX-4T-Ata was introduced into BL21 cells, fermented, and the GST-Ata fusion protein was purified, and then used as coating antigen. Diluted the coating antigen to 50 μg/mL with coating buffer (NaHCO$_3$ 29.3 g, Na$_2$CO$_3$ 19.5 g, dissolved with ddH$_2$O and constant volume to 1 L and adjusted the pH to 9.6), 100 μl/well, 4° C. overnight. Washed 3 times with PBST (1 L PBS added 500 μl Tween-20), patted dry, added 200 μl of PBST containing 5% (mass percentage) skimmed milk powder to each well, incubated at 37° C. for 2 h, then washed 3 times with PBST, patted dry, added multiple dilution of mouse serum of the immunized group obtained in the above 1 (diluted with PBST containing 5% (mass percentage) skimmed milk powder), 1000/well, and incubated at 37° C. for 60 min. Washed 3 times with PBST, patted dry, added donkey anti-mouse antibodies (Abcam, catalog number ab6820) (diluted by 1:10 000 with PBST containing 5% (mass percentage) skimmed milk powder), 1000 μl/well, incubated at 37° C. for 1 h. Washed 3 times with PBST, patted dry, added 1000 μl/well of OPD-H$_2$O$_2$ color developing solution, avoided light for color development for 15 min, added 50 μl of stop solution, and measured the OD$_{490}$ value.

Figure 3:
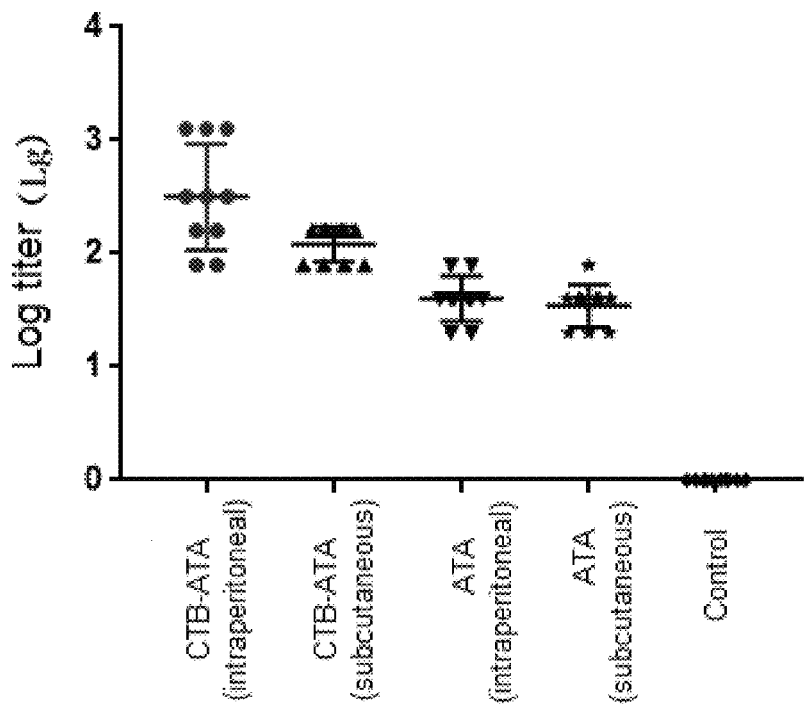
FIG. 3 is the titer results of antibody against *Acinetobacter baumannii* in the serum of each group of mice by indirect ELISA method test.

The results are shown in FIG. 3. It can be seen that the antibody titer after immunization with CTB-Ata fusion protein was higher than that of the Ata peptide group and the blank control group, and there was a significant difference. The antibody titer of intraperitoneal immunization with CTB-Ata fusion protein was highest, followed by antibody titer of subcutaneous immunization. It showed that the fusion protein CTB-Ata immunization can successfully make mice produce antibodies against *Acinetobacter baumannii*.

3. Mice Challenge Experiment 14 days after the last immunization, each mouse in each group (10 mice) was challenged by intraperitoneal injection with 1.5 times the LD$_{50}$ of *Acinetobacter baumannii*. Each mouse was injected with a volume of 200 μl. Observed and recorded the number of dead mice in each group for 7 consecutive days.

Figure 4:
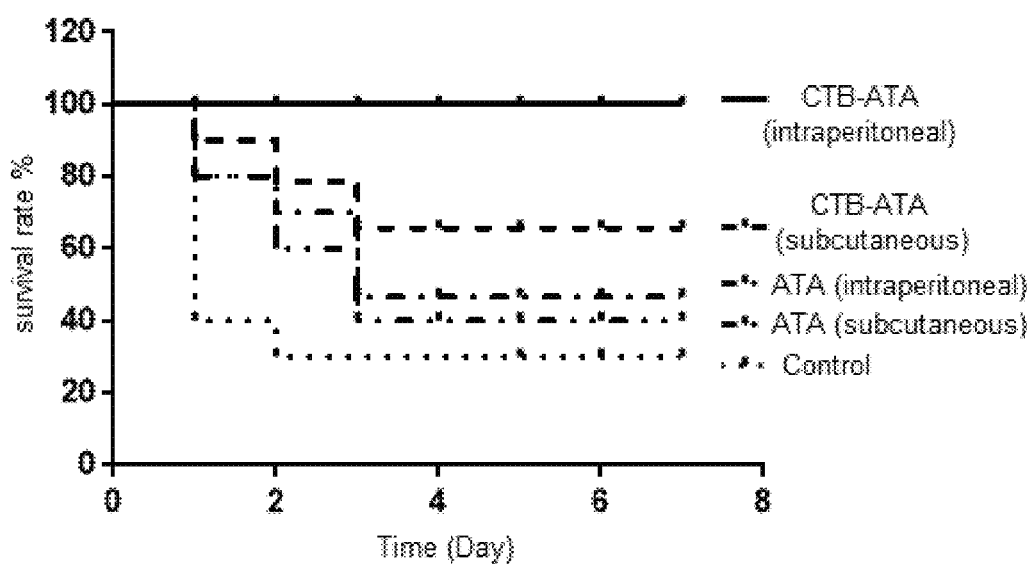
FIG. 4 is the experimental results of mice challenged with *Acinetobacter baumannii* after immunization with the fusion protein CTB-Ata.

The results are shown in FIG. 4. It can be seen that only 3 survived in the blank control group (control group), while all survived in the CTB-Ata intraperitoneal immunization group, and 7 survived in the CTB-Ata subcutaneous immunization group. Half of the mice in the Ata intraperitoneal immunization group without CTB assistance survived (5 mice), and 4 mice in the subcutaneous group survived. Therefore, it can be seen that the injection of the fusion protein CTB-Ata had a good protective effect on mice, indicating that the fusion protein CTB-Ata can be used to prevent diseases caused by *Acinetobacter baumannii*.

INDUSTRIAL APPLICATION

In the present invention, the 39 amino acids of the N-terminal α-helix part of surface protein Ata (*Acinetobacter* trimeric autotransporter) of *Acinetobacter baumannii* were taken and fused with CTB, and expressed in BL21. Purifying by a nickel column, and immunizing with 2.5 μg/mouse intraperitoneally or subcutaneously, which verified its immunogenicity and immunoprotection through the animal experiments, and proved that it has a good effect of anti-infection of *Acinetobacter baumannii*.

The protein was purified by a nickel column, and used to intraperitoneally or subcutaneously immunize mouses by 2.5 μg/mouse. Its immunogenicity and immunoprotection was verified through the animal experiments, which proves it has a good effect of anti-infection of *Acinetobacter baumannii*.

The invention claimed is:

1. A method for protecting animals or humans from infection of *Acinetobacter baumannii* or a method for preventing and/or treating with diseases caused by *Acinetobacter baumannii*, which comprises the following steps:
   immunizing a non-human animal or a human with a biomaterial to achieve resistance to *Acinetobacter baumannii* infection, wherein the biomaterial is one of the following:
   1) a protein consisting of 39 amino acids in the N-terminal α-helix part of the Ata protein transport functional domain of *Acinetobacter baumannii*;
   2) a protein composition consisting of 39 amino acids in the N-terminal α-helix part of the Ata protein transport functional domain of *Acinetobacter baumannii* and an adjuvant protein or a protein fragment with adjuvant function;
   3) a fusion protein consisting of 39 amino acids in the N-terminal α-helix part of the Ata protein transport functional domain of *Acinetobacter baumannii* and an adjuvant protein or a protein fragment with adjuvant function;
   wherein the amino acid sequence of said 39 amino acids in the N-terminal α-helix part of the Ata protein transport functional domain of *Acinetobacter baumannii* is shown as the amino acid residues 127-165 of SEQ ID NO: 2,
   wherein the fusion protein is any one of the following a)-c):
   a) the amino acid sequence consisting of the amino acid residues shown as SEQ ID NO: 2 in the sequence listing;
   b) a fusion protein obtained by attaching a tag to the N-terminal and/or C-terminal of the protein defined in a); and
   c) a protein whose amino acid sequence consists of the amino acid residues 20-165 of SEQ ID NO: 2 in the sequence listing.

2. The method according to claim 1, wherein:
the fusion protein has the amino acid sequence consisting of the amino acid residues shown as SEQ ID NO: 2 in the sequence listing.

3. The method according to claim 1, wherein:
the adjuvant protein is CTB protein.

* * * * *

SEQUENCE LISTING

<160> NUMBER OF SEQ ID NOS: 2

<210> SEQ ID NO 1
<211> LENGTH: 798
<212> TYPE: DNA
<213> ORGANISM: Artificial sequence
<220> FEATURE:
<223> OTHER INFORMATION: Synthesized

<400> SEQUENCE: 1

-continued

```
tctagatgca taattcgtgt cgctcaaggc gcactcccgt tctggataat gttttttgcg      60
ccgacatcat aacggttctg gcaaatattc tgaaatgagc tgttgacaat taatcatcgg     120
ctcgtataat gtgtggaatt gtgagcggat aacaatttca cacaggaaac agaattcatg     180
aagaaaattt ggctggcctt agccggcctg gttctggcat tcagcgccag cgcaaccccg     240
cagaacatca ccgacctgtg cgccgagtac cacaacaccc aaatttatac cctgaacgac     300
aaaattttta gctacaccga gagcctggca ggcaagcgcg agatggccat catcaccttc     360
aagaacggcg ccattttcca ggtggaggtg ccgggcagcc agcacatcga cagtcagaag     420
aaggccatcg agcgcatgaa ggacacccctg cgcatcgcct acctgaccga ggccaaggtg     480
gagaagctgt gcgtgtggaa caacaagacc ccgcacgcca tcgccgcaat cagcatggcc     540
aacggcggat ccggcaacaa aattaccaat ctgggtgatc agttacaaca agtgttctat     600
gacaccaata aacgtattga tgacgttgag aaaaaagcta atgcaggtat tgccgctgcc     660
atggccttag aaggcggttc tggtagcgcc gtgaccgagt actatctgaa ccatggcgag     720
tggccgggta ataacaccag cgccggcgtg ccacaagca gtgagatcaa gctcgagcac     780
caccaccacc accactga                                                   798
```

<210> SEQ ID NO 2
<211> LENGTH: 206
<212> TYPE: PRT
<213> ORGANISM: Artificial sequence
<220> FEATURE:
<223> OTHER INFORMATION: Synthesized

<400> SEQUENCE: 2

```
Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Gly Gly Ser Gly Asn Lys
        115                 120                 125

Ile Thr Asn Leu Gly Asp Gln Leu Gln Gln Val Phe Tyr Asp Thr Asn
    130                 135                 140

Lys Arg Ile Asp Asp Val Glu Lys Lys Ala Asn Ala Gly Ile Ala Ala
145                 150                 155                 160

Ala Met Ala Leu Glu Gly Gly Ser Gly Ser Ala Val Thr Glu Tyr Tyr
                165                 170                 175

Leu Asn His Gly Glu Trp Pro Gly Asn Asn Thr Ser Ala Gly Val Ala
            180                 185                 190

Thr Ser Ser Glu Ile Lys Leu Glu His His His His His
        195                 200                 205
```